United States Patent [19]
Daher et al.

[11] Patent Number: 5,656,293
[45] Date of Patent: Aug. 12, 1997

[54] DELIVERY SYSTEM FOR ENHANCED ONSET AND INCREASED POTENCY

[75] Inventors: Lawrence J. Daher, Elkhart; Manley A. Paulos, Granger, both of Ind.

[73] Assignee: Bayer Corporation, Pittsburgh, Pa.

[21] Appl. No.: 398,722

[22] Filed: Mar. 6, 1995

Related U.S. Application Data

[62] Division of Ser. No. 908,527, Jun. 29, 1992, Pat. No. 5,424,075.

[51] Int. Cl.$^6$ .................................................. A61K 9/20
[52] U.S. Cl. .......................... 424/465; 424/489; 424/466; 424/464
[58] Field of Search .......................... 424/439, 466, 424/465, 464, 468; 514/415

[56] References Cited

U.S. PATENT DOCUMENTS

| | | | |
|---|---|---|---|
| 4,855,314 | 8/1989 | Oxford et al. | 514/415 |
| 5,292,518 | 3/1994 | Kuhrts | 424/439 |
| 5,424,075 | 6/1995 | Daher et al. | 424/465 |

OTHER PUBLICATIONS

Merck Index, Eleventh Edition, Page(s) 1291, Item #8126 Year Published 1989.

*Primary Examiner*—Thurman K. Page
*Assistant Examiner*—William E. Benston, Jr.
*Attorney, Agent, or Firm*—Mary G. Boguslaski

[57] ABSTRACT

The invention discloses a swallow tablet which is capable of disintegrating within less than about fifteen minutes and providing fast delivery of therapeutic drugs. The delivery system is composed of between 0.250 and 1.0 Gm of an alkali metal or alkaline-earth metal salt of an edible organic acid. A preferred delivery system is trisodium citrate.

1 Claim, 4 Drawing Sheets

DELIVERY SYSTEM FOR ENHANCED ONSET AND INCREASED POTENCY

This is a division of application Ser. No. 07/908,527, filed on Jun. 29, 1992, now U.S. Pat. No. 5,424,075.

FIELD OF THE INVENTION

The invention relates to a delivery system for therapeutic drugs which may be incorporated into a solid dosage form to provide a swallowable tablet. Specifically the invention relates to the use of salts of edible organic acids in combination with a therapeutic drug.

BACKGROUND OF THE INVENTION

Previously it has been shown that effervescent dosage forms may provide faster action for some drugs. This was often attributed to the fact that such dosage forms were dissolved in water prior to ingestion and therefor the drug was in solution and readily available for absorption.

However, the effervescent delivery system has been unsatisfactory for some consumers; and can present formulators with difficult taste masking problems.

It has now been found that the fast delivery of an effervescent system, with an enhanced onset of action, may be provided in a solid oral dosage form as a swallowable tablet.

DESCRIPTION OF THE DRAWINGS

The Figures relate to Example 1 where ranitidine was administered to dogs with a delivery system composed of trisodium citrate and bicarbonate.

SUMMARY OF THE INVENTION

Figure 1:
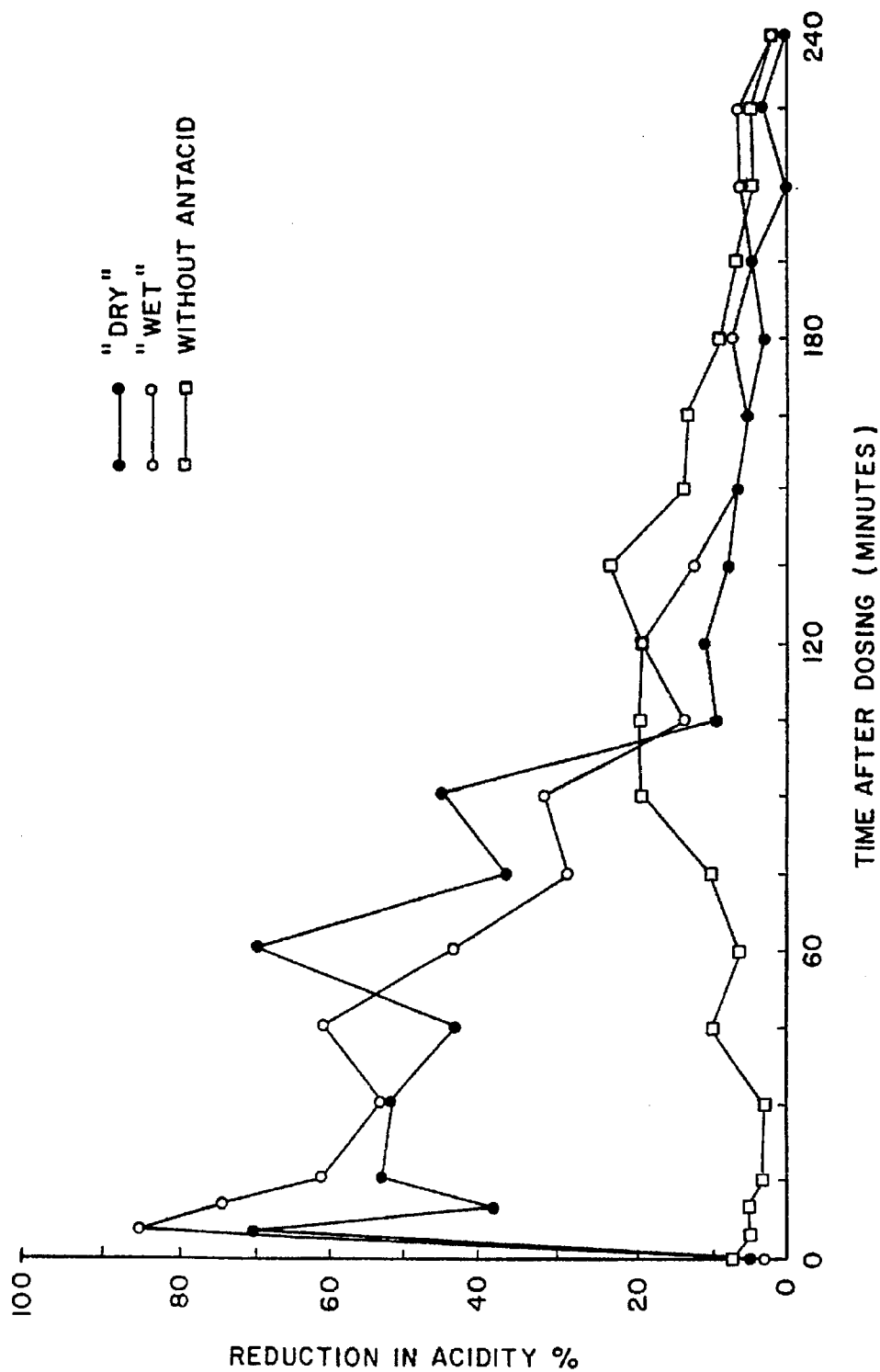
FIG. 1 is a graph of the reduction in tritratable acidity (percent) versus time after dosing (minutes) comparing the activity of the solid dosage form ("DRY") and an effervescent dosage ("WET") of the same concentration (0.3 mg/kg) and the same acid neutralizing capacity of 16 milliequivalents (mEq). The squares show the control dosage (i.e. without antacid).

The invention provides a delivery system for enhanced onset and increased potency of therapeutic drugs. The delivery system plus therapeutic may be provided in a solid oral dosage form, such as a swallow tablet. The delivery system comprises an effective amount of therapeutic drug and salt of an edible organic acid, wherein the salt is present in an amount of between 0.250 Gm and 1.0 Gm per tablet with at least about 0.5 Gm salt per dose. The edible organic acid is chosen from the group consisting of citric, malic, fumaric, tartaric and succinic acid or mixtures thereof. The salt is an alkali metal salt or an alkaline-earth metal salt or mixtures thereof. Therapeutic drugs of particular interest are chosen from the group consisting of analgesics, $H_2$ Blockers and sympathomimetic amine drugs. The delivery system is preferably composed of trisodium citrate and may additionally contain a carbonate or bicarbonate.

DESCRIPTION OF THE INVENTION

The invention provides a solid oral dosage form which may be swallowed. The tablet will disintegrate in vivo within about fifteen minutes and provide enhanced onset of action over previous solid oral dosage forms on the order of the enhanced onset seen with the effervescent delivery system. It is speculated, though not relied on, that the delivery system disclosed herein provides rapid stomach emptying on the order of that seen previously only with effervescent systems which are dissolved and ingested as liquids. This rapid stomach emptying gets the active drug to the site of absorption faster than previous solid dosage forms and therefore provides for a more rapid onset of action and increased potency.

The delivery system is composed of a salt of an edible organic acid in an amount of at least about 0.5 Gm per dose. Practical limits on tablet size means that a tablet could contain materials up to a total of about 1.5 Gm, which must include the salt, active drug and all other materials required for tabletting. A one tablet dose would contain from about 0.5 GM to about 1.0 Gm acid salt. If two tablets are to provide a dose, a single tablet could contain from about 0.25 Gm to about 1.0 Gm.

Edible organic acids useful in the invention are citric acid, malic acid, fumaric acid, tartaric acid, succinic acid and the like or mixtures thereof. Most preferred is citric acid. Useful salts include the alkali metal salts and alkali-earth metal salts of these acids such as sodium, potassium, calcium or magnesium or mixtures thereof. A preferred salt is trisodium citrate.

The composition may also contain a carbonate or bicarbonate to facilitate disintegration, or other such disintegrants. In addition, other excipients, useful in the art of tabletting, such as lubricants, binders, buffers, antioxidants, and colorants may be used. The tablet may be coated with a thin layer of a protective coating to provide a dustless and easily swallowed dosage form which is well known to those of skill in the art.

In addition to the delivery system and excipients, the solid dosage form would contain an effective amount of an active drug substance. This amount may be the therapeutically effective amount commonly used in prescription dosage forms, or may, because of the efficacy of the delivery system provided herein, be a reduced amount. Preferred therapeutics include those from the classes of analgesics, $H_2$ Blockers and sympathomimetic amine drugs (commonly referred to as decongestants).

In particular, the dosage form is useful with analgesics chosen from the group consisting of aspirin, acetaminophen, ibuprofen and ketoprofen; $H_2$ Blockers chosen from the group consisting of ranitidine, famotidine, cimetidine and nizatidine; and the sympathomimetic amine drugs chosen from the group consisting of phenylpropanolamine, phenylephrine and pseudoephridine. Because of the ability of this delivery system to provide enhanced onset and increased potency (synergy), a lower dose than that used with a prescription dosage in the traditional tablet forms presently available, may be used. Therefore, this swallow oral dosage form will be particularly useful for over-the-counter medications.

The composition may be provided as a capsule, tablet or caplet or other solid oral dosage form.

A preferred method of preparing the granulate for the oral dosage form may be used generally to prepare granulates of sodium salts of acidic therapeutic drugs of limited water solubility. The acidic therapeutic drug of interest is mixed with anhydrous trisodium citrate to form a dry mixture; to the dry mixture is added a near saturated aqueous solution of trisodium citrate to form an overwet granulation mixture. A near saturated solution of trisodium citrate is approximately 40% by weight trisodium citrate. An overwet mixture is a mixture that is wetter than commonly used by those of skill in the art to prepare granulates. It may be termed "more than damp" and is wet enough for a chemical reaction to take place between the citrate and the drug. An overwet mixture may be described as doughy or may even approach a paste-like consistency. The overwet granulation mixture is then mixed for a time sufficient to allow the anhydrous trisodium citrate to hydrate, forming a mixture dry enough to granulate. The hydrated mixture is then granulated as is standard to the art.

The following examples disclose preferred embodiments of the invention, but do not limit the applicability of the invention which is solely defined by the claims.

EXAMPLES

Example 1

Ranitidine

This study was designed to test the activity of a dry formulation of Effervescent Antacid Base (EAB, described below) plus ranitidine combination and to compare its effectiveness with that of the previously tested wet formulations (those dissolved in water prior to ingestion). The combination of 0.3 mg/kg ranitidine+16 mEq EAB was selected for testing.

Studies monitored gastric secretion in gastric fistula beagle dogs. Beagle dogs were dosed with two capsules containing (in total) 1.273 mg trisodium citrate (2 $H_2O$), 575 mg heat treated sodium bicarbonate plus 0.3 mg/kg of the $H_2$ Blocker ranitidine (as per individual weight of each Beagle). This dosage of ranitidine (administered without the effervescent antacid base or sodium citrate) had been shown previously to be ineffective as an anti-secretory agent for such dogs. Altogether 8 trials (8 dogs) were performed. In previous trials with "WET" dosage forms, ranitidine with the effervescent antacid base was dissolved and administered to dogs via gastric fistula. In these trials, the test formulation was not dissolved in water and was not administered as a solution via the gastric fistula. Instead, for each dog, the appropriate amounts of dry ingredients were mixed and divided into two capsules. The capsules were given orally to the dogs and washed down by placing small amounts of water on tongue via a syringe filled with 28 mL. About half the syringe content was used for washing down; content remaining was administered to dog via fistula. Thus, amounts of all constituents including water, were the same as used in previous tests.

Figure 2:
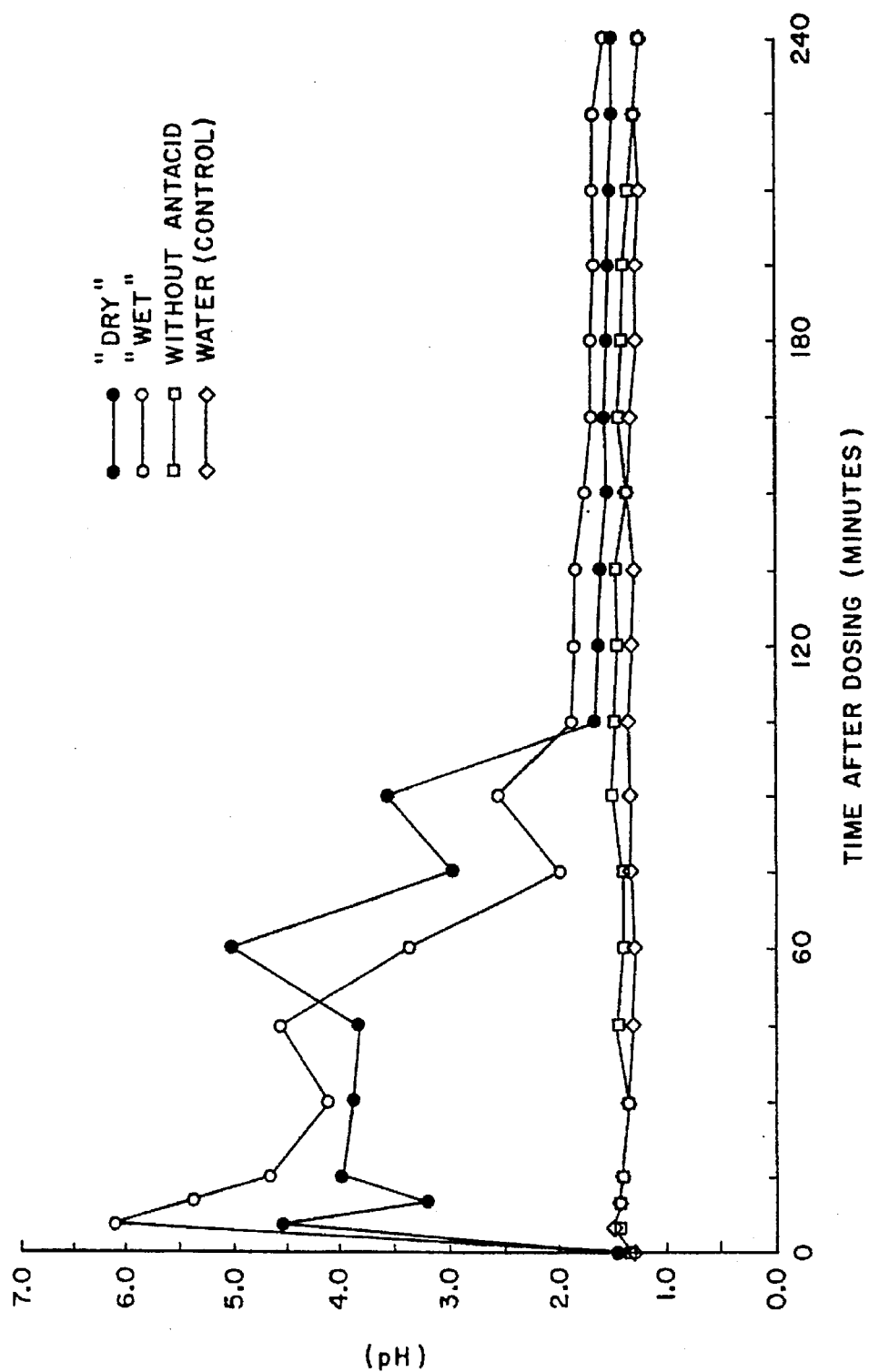
FIG. 2 is a graph of the gastric acidity (pH) versus time after dosing (minutes) comparing the activity of the solid dosage form ("DRY") and an effervescent dosage ("WET") of the same concentration (0.3 mg/kg) and the same acid neutralizing capacity of 16 milliequivalents. The squares show the control dosage (i.e. without antacid) and the triangles show the administration of water.

Results show that the effect of the two dosage forms is practically identical. A comparison of the effects of the two formulations on titratable acidity are presented in FIG. 1, and a comparison of the effects on pH are presented in FIG. 2. Inspection of these figures reveals that results of the present test with dry formulation, almost exactly duplicate the results of the previous tests with wet formulation. Within the limits of these tests, no significant differences between the two formulations can be discerned.

Figure 3:
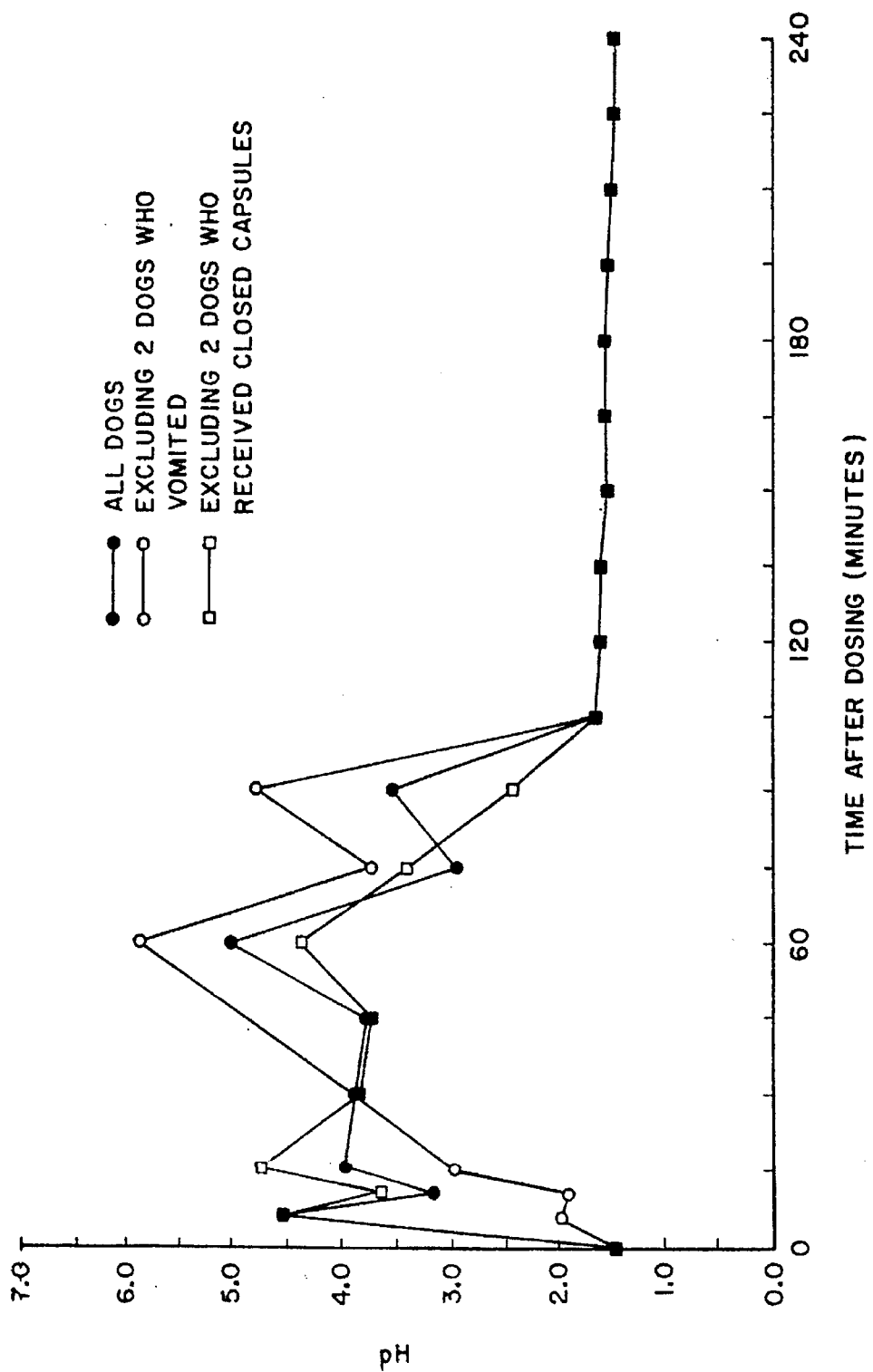
FIG. 3 is a graph of the gastric acidity (pH) versus time after dosing (minutes) of the solid dosage form ("DRY") showing the effect on dogs.
Figure 4:
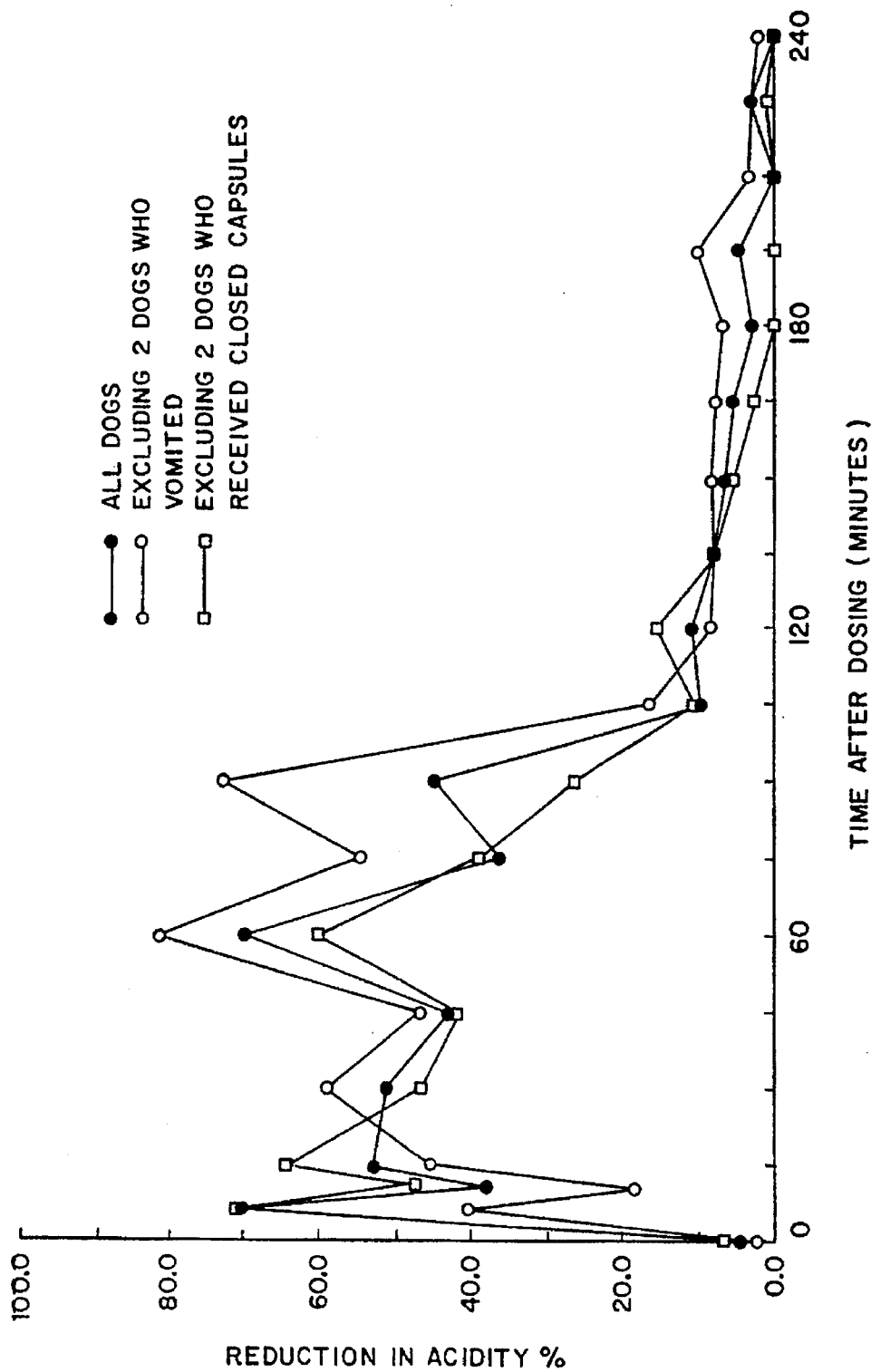
FIG. 4 is a graph of the reduction in tritratable acidity (percent) versus time after dosing (minutes) of the solid dosage form ("DRY") showing the effect on dogs.

Because 2 of the 8 dogs tested received closed capsules instead of open capsules, and because 3 of the dogs tested experienced vomiting during the test, the influence of these variables needed to be examined. Thus, the means for all dogs were compared to the means for only those dogs which received closed capsules (FIG. 3), and were compared to the means for only those dogs which did not vomit (FIG. 4).

These comparisons reveal that, regardless of the variables of capsule closure or vomiting, the apparent equivalency of the two dosage forms remains definitely established.

The results showed that the ranitidine with the delivery system of the invention was significantly more effective than would be expected from a solid oral dosage form (See FIG. 1–4). The figures demonstrate that a synergistic effect was produced when ranitidine, at an otherwise ineffective dose, combined with the delivery system utilized in these experiments and administered in a solid oral dosage form.

Similar results were obtained when ranitidine was administered to Beagles with a sodium citrate delivery system (not including a carbonate or bicarbonate).

Example 2

Acetaminophen Swallow Tablet Formulation

Formula 001

| mg/tab | Ingredients | Total Quantities |
|---|---|---|
| 361.11 | Acetaminophen 90% (Compap L) | 108.33 Gm |
| 648.11 | Formula 169 (see below) | 194.67 Gm |
| 48.39 | Sodium Starch Glycolate | 14.52 Gm |
| 0.10 | Docusate Sodium, Sodium Benzoate (85:15) | 0.03 Gm |
| 20.00 | Crospovidone (Polyplasdone XL) | 6.00 Gm |
| 1.50 | Magnesium Stearate | 0.45 Gm |
| 1080.00 | | 324.00 Gm |

Pass all ingredients thru a #24 mesh screen to delump.

Add all together except the Magnesium Stearate and mix in a V-Blender for 7 minutes.

Add the Magnesium Stearate and blend for another 3 minutes.

Compress into tablets using 0.344"×0.750" capsule shaped tooling.

Formula 169

| % W/W | Ingredients | Total Quantities |
|---|---|---|
| 7.0 | Starch 1500 | 140 Gm |
| 93.0 | Trisodium Citrate Dihydrate | 1860 Gm |
| 100.0 | | 2000 Gm |

Add powders to a 8 quart V-Blender with Intensifier Bar.

Dry mix with Intensifier Bar turned on for 3 minutes.

Wet granulate using 193 Gm of Water.

Discharge and pass thru a #24 mesh screen.

Dry in hot air oven at 130 F. overnight, (ca. 16 hours).

Dry size by passing thru a #24 mesh screen.

Example 3

Aspirin Swallow Tablet Formulation

| mg/tab | Ingredients | Total Quantities |
|---:|---|---:|
| 362.0 | Aspirin & Starch Granulation 90% | 72.4 Gm |
| 700.0 | Formula 169 (See Example 2) | 140.0 Gm |
| 50.0 | Sodium Starch Glycolate | 10.0 Gm |
| 20.0 | Crospovidone (Polyplasdone XL) | 4.0 Gm |
| 60.0 | Formula 038* | 12.0 Gm |
| 18.0 | Formula 171* | 3.6 Gm |
| 1210.0 | | 242.0 Gm |

Dry Sodium Starch Glycolate and Crospovidone in hot air oven at 130° F. overnight, (ca. 16 hours).

Add all ingredients to a V-Blender and mix for ten minutes.

Compress into tablets using 0.344"×0.750" capsule shaped tooling.

*Formula 038

| % W/W | Ingredients | Total Quantities |
|---:|---|---:|
| 6.0 | Polyethylene Glycol 8000 | 30.0 Gm |
| 94.0 | Trisodium Citrate, Anhydrous Powder | 470.0 Gm |
| 100.0 | | 500.0 Gm |

Blend powders together and then pass them thru a 4" Air Mill (micronizer).

*Formula 171

| % W/W | Ingredients | Total Quantities |
|---:|---|---:|
| 0.2 | Dioctyl Sodium Sulfosuccinate (DOSS) | 1.0 Gm |
| 99.8 | Calcium Sorbate | 500.0 Gm |
| 100.0 | | 501.0 Gm |

Prepare 200 Gm of 0.5% w/w DOSS from Complemix-50 (50% DOSS) by mixing together 2 Gm of Complemix-50 and 198 Gm of water.

Add the calcium sorbate to the pot of a Hobart Tabletop Mixer and add the 200 Gm of DOSS solution to it while mixing.

With continued mixing add an additional 135 Gm of water.

Discharge the dampened powder and dry it in a hot air oven at 130° F. overnight, (ca. 16 hours).

Pass the dried powder thru a #60 mesh screen.

Example 4

Ibuprofen Swallow Tablet Formulation

Formula 182

| mg/tab | Ingredients | Total Quantities |
|---:|---|---:|
| 792.0 | Formula 144* | 158.4 Gm |
| 60.0 | Sodium Starch Glycolate | 12.0 Gm |
| 45.0 | Formula 038 (see Example 3) | 9.0 Gm |
| 14.0 | Formula 171 (see Example 3) | 2.8 Gm |
| 911.0 | | 182.2 Gm |

Add all ingredients to a bottle, cap it, and mix the contents for 10 minutes using a Turbula Mixer.

Compress into tablets using 0.344"×0.700" capsule shaped tooling.

*Formula 144

Pass a quantity of Ibuprofen thru a #24 mesh screen to delump it.

Prepare a powder mixture of 200.0 Gm of Ibuprofen and 400.0 Gm of Trisodium Citrate, Anhydrous Powder by mixing them together in the pot of a Tabletop Hobart Mixer.

Prepare a 400 Gm quantity of 40% w/w solution of Trisodium Citrate Dihydrate in Water by dissolving 160 Gm of it in 240 Gm of Water.

With the Hobart Mixer running at slow speed, pour in 338 Gm of the 40% solution all at once, on top of the Ibuprofen and Trisodium Citrate mixture.

Continue mixing for 20 minutes.

Discharge and pass thru a #24 mesh screen.

Dry in hot air over at 130° F. overnight, (ca. 16 hours).

Dry size by passing thru a #24 mesh screen.

792 mg of the dried granulation provides 200 mg of Ibuprofen in water soluble form, and 592 mg of Trisodium Citrate Dihydrate.

Example 5

Ketoprofen Swallow Tablet Formulation

| mg/tab | Ingredients | Total Quantities |
|---:|---|---:|
| 110.0 | Formula 118* | 22.0 Gm |
| 700.0 | Formula 169 (see Example 2) | 140.0 Gm |
| 60.0 | Sodium Starch Glycolate | 12.0 Gm |
| 20.0 | Crospovidone (Polyplasdone XL) | 4.0 Gm |
| 45.0 | Formula 038 (see Example 3) | 9.0 Gm |
| 14.0 | Formula 171 (see Example 3) | 2.8 Gm |
| 949.0 | | 189.8 Gm |

Add all ingredients to a bottle, cap it, and mix the contents for 10 minutes using a Turbula Mixer.

Compress into tablets using 0.344"×0.700" capsule shaped tooling.

*Formula 118

Weight 2.0 Gm of Decaglycerol Tetraoleate (Caprol 10 G 4 0) into a 140 mL beaker. Add 98.0 Gm of water and mix with a Lighnin Mixer until all of the Caprol is dispersed.

Add 50.0 Gm of Ketoprofen and 150.0 Gm of Trisodium Citrate, Anhydrous Powder to a large mortar and pestle, and triturate until well mixed.

Add 85.2 Gm of the Caprol dispersion all at once to the powder mixture and triturate thoroughly, first forming a sticky paste which begins to dry up in a few minutes.

Knead the soft mass with the hands, and when it begins to get crumbly, pass it thru a #24 mesh screen.

Dry in hot air oven at 130° F. overnight, (ca. 16 hours).

Dry size by passing thru a #24 mesh screen.

110 mg of the dried granulation provides 25 mg of Ketoprofen in water soluble form, and ca. 85 mg of Trisodium Citrate Dihydrate.

Example 6

Ranitidine Swallow Tablet Formulation

| mg/tab | Ingredients | Total Quantities |
|---|---|---|
| Formula 188 | | |
| 140.0 | Formula 181* | 28.0 Gm |
| 635.0 | Formula 169 (see Example 2) | 127.0 Gm |
| 135.0 | Starch 1500 | 27.0 Gm |
| 5.0 | Magnesium Stearate | 1.0 Gm |
| 5.0 | Formula 171 (see Example 3) | 1.0 Gm |
| 5.0 | Silicon Dioxide (Syloid 244FP) | 1.0 Gm |
| 925.0 | | 185.0 Gm |

*Formula 181

| % W/W | Ingredients | Total Quantities |
|---|---|---|
| 10.0 | Ranitidine Hydrochloride | 50.0 Gm |
| 10.0 | Calcium Acetate Powder | 50.0 Gm |
| (Trace) | Mixed Tocopherols | (Trace Amt.) |
| 80.0 | Mannitol Powder | 400.0 Gm |
| 100.0 | | 500.0 Gm |

Prepare a 0.1% solution of Covi-Ox T-30P (dried mixed tocopherol concentrate) in water.

Pass the powders thru a #24 mesh screen to delump.

Add them to the pot of a Hobart Tabletop Mixer, and while mixing add 30 Gm of the Covi-Ox Solution.

Pass the wet granulate thru a #24 mesh screen and dry it in a hot air oven at 130° F. overnight, (ca. 16 hours).

Dry size by passing thru a #24 mesh screen.

Example 7

Pseudoephedrine Swallow Tablet Formulation

| mg/tab | Ingredients | Total Quantities |
|---|---|---|
| 20.0 | Pseudoephedrine Hydrochloride | 4.0 Gm |
| 800.0 | Formula 169 (see Example 2) | 160.0 Gm |
| 240.0 | Sodium Bicarbonate, Heat Treated | 48.0 Gm |
| 75.0 | Sodium Starch Glycolate | 15.0 Gm |
| 25.0 | Crospovidone (Polyplasdone XL) | 5.0 Gm |
| 6.0 | Magnesium Stearate | 1.2 Gm |
| 6.0 | Formula 171 (see Example 3) | 1.2 Gm |
| 6.0 | Silicon Dioxide (Syloid FP) | 1.2 Gm |
| 1178.0 | | 235.6 Gm |

Pass all ingredients thru a #24 mesh screen to delump.

Add all ingredients to a bottle, cap it, and mix the contents for 10 minutes using a Turbula Mixer.

Compress into tablets using 0.344"×0.750" capsule shaped tooling.

It should be understood that many modifications and variations can be made in the proportions and components used herein without departing from the spirit and scope of the invention, which is solely defined by the claims.

What is claimed is:

1. A method of preparing a granulate of a sodium salt of an acidic therapeutic drug of limited water solubility for use in dosage forms which require high water solubility, comprising the steps of:

(a) mixing an acidic therapeutic drug of limited water solubility with anhydrous trisodium citrate to form a dry mixture;

(b) adding a near saturated aqueous solution of trisodium citrate to the dry mixture to form an overwet granulation mixture;

(c) mixing the overwet mixture for a time sufficient to allow the anhydrous trisodium citrate to hydrate, forming a mixture dry enough to granulate; and (d) granulating the hydrated mixture.

* * * * *